United States Patent [19]

Adachi et al.

[11] 4,396,631

[45] Aug. 2, 1983

[54] BIFIDOBACTERIUM-CONTAINING CONFECTIONERY TABLETS AND PROCESS FOR PREPARING THE SAME

[75] Inventors: Takashi Adachi, Yokohama; Takeo Ooki, Chiba; Takahiko Hayashi, Sagamihara; Kazuo Yoshida, Yokohama, all of Japan

[73] Assignee: Meiji Seika Kaisha Ltd., Tokyo, Japan

[21] Appl. No.: 241,514

[22] Filed: Mar. 9, 1981

[30] Foreign Application Priority Data

Apr. 8, 1980 [JP] Japan ................... 55-45245

[51] Int. Cl.$^3$ ............................ A23G 3/00; C12R 1/01
[52] U.S. Cl. ....................................... 426/61; 426/71; 426/801; 426/454; 426/661; 435/253; 435/822; 424/93; 424/94
[58] Field of Search ............... 426/801, 61, 71, 454, 426/661; 424/93, 94; 435/253, 822

[56] References Cited

U.S. PATENT DOCUMENTS

| | | | |
|---|---|---|---|
| 2,611,706 | 9/1952 | Bernhart et al. | 426/801 |
| 2,694,640 | 11/1954 | György et al. | 426/801 |
| 2,697,663 | 12/1954 | Tomarelli | 426/801 |
| 2,783,148 | 2/1957 | György et al. | 426/801 |
| 2,811,450 | 10/1957 | Petuely | 435/253 |
| 2,872,382 | 2/1959 | Keck | 426/801 |
| 3,677,897 | 7/1972 | Jefferys | 435/253 |
| 3,897,307 | 7/1975 | Porubcan | 435/253 |

FOREIGN PATENT DOCUMENTS

| | | | |
|---|---|---|---|
| 41-32908 | 5/1966 | Japan | 426/801 |
| 6710511 | 1/1968 | Netherlands | 426/801 |

*Primary Examiner*—Jeanette M. Hunter
*Attorney, Agent, or Firm*—Frishauf, Holtz, Goodman & Woodward

[57] ABSTRACT

Disclosed is a bifidobacterium-containing confectionery tablet, and a process for preparing the same, which is prepared by mixing a freeze-dried living bifidobacterium powder to a basic compounding material separately prepared in a powdery state and forming a tablet of said powdery mixture, comprising further adding to the mixture of said basic compounding material and said bifidobacterium powder one or more of substances selected from the group consisting of starch, starch hydrolyzate and protein, containing not more than 4% of water.

8 Claims, No Drawings

BIFIDOBACTERIUM-CONTAINING CONFECTIONERY TABLETS AND PROCESS FOR PREPARING THE SAME

This invention relates to a confectionery tablet capable of preserving therein a dried bifidobacterium in a stable state for a long period, and also relates to a process for the preparation of the bifidobacterium-containing confectionery tablet.

The bifidobacterium is well known as a bacterium constituting a large portion of the intestinal bacteria living in a breast-fed infant. There have been reported a great number of studies on the physiological significance of the bifidobacterium; for example, broadly known are effects such as the inhibiton of putrefaction induced by putrefying intestinal bacteria, inhibition of the production of toxic amine compounds, and the inhibition of the growth of pathogenic bacteria by the production of organic acids such as lactic acid and acetic acid.

In other aspects, it is known that the bifidobacterium can be incorporated into foods. In the production of processed milk drink, for instance, the bifidobacterium is cultured in an appropriate medium, collected by centrifuge, and incorporated into milk or fermented milk in the state of the living bacterium. The incorporation of the bifidobacterium, however, has a certain drawback, that is, in addition to the known malodor inherent to bifidobacterium, the food containing the bifidobacterium is necessarily stored at a temperature of not more than 10° C. to keep the number of living bacteria at a certain level and also for preventing the undesirable production of acids and the deterioration of taste caused by secondary fermentation. Moreover, the bifidobacterium-containing food can be stored only for a short period of few weeks even if it is kept under the above-mentioned condition, and must be abandoned once it was denatured.

As a result of intensive studies for producing a bifidobacterium-containing food which does not have the aforenoted drawbacks which are inherently present in the conventional bifidobacterium-containing foods, which does not have the malodor inherent in the bifidobacterium, which satisfies the public taste, which has stability enabling storage for long period which avoids the necessity of a specifically designed apparatus, and which is of a nature enabling ingestion at all times, the present inventors have found that the above described drawbacks are obviated by providing a confectionery tablet which is prepared by incorporating the dry bifidobacterium into a compounding material containing at least 1% of one or more of substances selected from the group consisting of starch, starch hydrolyzate and protein, containing not more than 4% of water.

In the conventional process for incorporating a microorganism into a confectionery tablet, the living microorganism is dried, reduced to powder, added to a basic compounding material for the formation of tablet such as sugar, and then molded into tablet by means of a tablet machine. However, it is not practical to apply this conventional process to the formation of the bifidobacterium-containing confectionery tablet, because, in order to ensure the number of the living bifidobacteria in the confection for a long period at a certain level, the confectionery tablet must be stored at a low temperature due to the unsatisfactory stability of the bifidobacterium. To solve such problem, the process in the present invention is characterized by adding to a mixture of the aforementioned basic compounding material and a freeze-dried bifidobacterium powder one or more pre-dried substances selected from the group consisting of starch, starch hydrolyzate and protein, containing not more than 4%, preferably not more than 0.2 to 1%, of water, in a desired amount.

Accordingly, in the present invention, there is provided a bifidobacterium-containing confectionery tablet composed of a basic compounding material with a dry bifidobacterium incorporated therein, which comprises said confectionery tablet further including one or more of substances selected from the group consisting of starch, starch hydrolyzate and protein, containing not more than 4% of water. Also provided is a process for preparing a bifidobacterium-containing confectionery tablet by mixing a freeze-dried living bifidobacterium powder to a basic compounding material separately prepared in a powdery state and forming a tablet of said powdery mixture, which comprises further adding to the mixture of said basic compounding material and said bifidobacterium powder one or more substances selected from the group consisting of starch, starch hydrolyzate and protein, containing not more than 4% of water.

Preferred examples of the basic compounding materials employed in the present invention include saccharides with low water content, such as granulated sugar, hard sugar, milk sugar and glucose; and crystalline materials of organic acids such as citric acid, succinic acid, ascorbic acid and tartaric acid. Other compounding materials similar to the above-exemplified materials that are conventionally employed for compounding to form confectionery tablets can be also used. These basic compounding materials are reduced to powder and dried with or without any other appropriate processing. If desired, other additives such as flavor can be incorporated.

Examples of the starch to be added to the basic compounding material include potato starch, sweet potato starch and corn starch. Examples of the starch hydrolyzate include dextrin, powdered starch syrup and maltose which are produced by hydrolyzing the above-mentioned starch with an acid or enzyme to reach a level of not more than DE 35. Examples of the proteins include proteins such as defat milk, casein and soybean protein, and edible materials containing these proteins as the principal components. The material can be compounded singly or in the form of a mixture. The water content of these substances should be not more than 4%, and more preferably 0.2 to 1%, as aforementioned.

Examples of the bifidobacteria employed in the present invention include *Bifidobacterium infantis*, *Bifidobacterium longum*, and *Bifidobacterium adolescentis*. Other strains can be employed as long as they belong to the genus bifidobacterium. These bacteria are publicly known and can be obtained easily. The strain is anaerobically cultured in a conventional manner, and the bacterial mass is collected by a conventional means, such as centrifuge, after completion of the culturing process. The so obtained bacterial mass is employed as such in the dry form, or after incorporation into a dispersing medium, such as skim milk, under anaerobical conditions to form a dry dispersion. Freeze-drying is preferably employed for the drying procedure and the water content after completion of the drying is preferably adjusted to a level of not more than about 3%. The dried mass is then reduced to powder by an appropriate method for facilitating the mixing procedure. The dried bacterial mass can be diluted with the aforementioned dehydrated-and-dried material(s) to adjust the number of the living bacteria contained in one gram of the powder so that the initial number of the bacteria in the product may be readily adjusted to a constant level.

The ratio for forming mixture of the aforementioned basic compounding material, the additive such as starch, and the dry bifidobacterium powder is generally in the range of from 98.8:1.0:0.2 to 84.8:15.0:0.2. The said additive is in an amount not less than 1% based on the total amount of the mixture and is preferably in an amount between 3 and 15%. There is required no specific conditions on the process for forming the mixture. For instance, a conventional mixer is employed to mix them homogeneously. The formation of tablets can be done in a batch-type tablet machine, but the rotary tablet machine is preferably employed for enabling continuous formation of tablets.

The confectionery tablets produced by the present invention have no malodor inherently adhered to the bifidobacterium and are of long storage life. Accordingly, the confectionery tablets can be orally taken as such or in a mixture with other foods at an optional time and at an optional dosage. Thus, all of the problems in the conventional bifidobacterium-containing foods are now eliminated by the present invention.

The above description is incidentally directed to the tablet form. However, the effects of the present invention are also observed even in the form of powdery tablets, and the confection is likewise provided in the form of packed powder, if desired.

The present invention is illustrated by the following experimental results:

To a basic compounding material containing 0.2 part of a bifidobacterium powder produced by the cultivation and freeze-drying was added a starch or other additives adjusted in advance to have the varied water content (as indicated in Table 2), to prepare a mixed material of ratio as indicated in Table 1. The thus mixed material was molded into tablet and stored at 37° C. for 3 months to observe the number of the living bacteria. The results are shown in Table 2.

TABLE 1

| Experimental section | Basic compounding material | Additive such as starch |
|---|---|---|
| A | 99 | 1 |
| B | 97 | 3 |
| C | 93 | 7 |
| D | 85 | 15 |
| Control | 100 | — |

TABLE 2

| Additive | Water content after drying (%) | Experimental section A | B | C | D |
|---|---|---|---|---|---|
| Corn Starch | 0.5 | $1.0 \times 10^6$ | $1.9 \times 10^7$ | $7.6 \times 10^7$ | $1.6 \times 10^8$ |
| Dextrin (DE 12) | 0.4 | $2.0 \times 10^6$ | $2.6 \times 10^7$ | $7.3 \times 10^7$ | $1.2 \times 10^8$ |
| Dextrin (DE 35) | 0.2 | $4.8 \times 10^6$ | $6.3 \times 10^7$ | $6.6 \times 10^7$ | $1.6 \times 10^8$ |
| Dextrin (DE 2) | 0.3 | $1.0 \times 10^6$ | $1.6 \times 10^7$ | $9.2 \times 10^7$ | $1.3 \times 10^8$ |
| Maltose (DE 55) | 4.0 | $7.2 \times 10^5$ | $1.0 \times 10^6$ | $5.5 \times 10^6$ | $1.5 \times 10^7$ |
| Defat Milk | 1.0 | $5.2 \times 10^5$ | $4.3 \times 10^7$ | $1.2 \times 10^7$ | $1.0 \times 10^8$ |
| Control | | | $1.0 \times 10^5$ | | |

Remarks:
The number of the living bifidobacteria indicated in Table 2 is based on 1 g. of the confectionery tablet. The number of the living bifidobacteria at the initial stage of the experiment was $1.6 \times 10^8$/g. of the confectionery tablet.

As seen from the above Table 2, the experimental sections where there was added corn starch, dextrin, maltose or defat milk showed no significant decrease of the number of the living bacteria, while the control section where there was added no such additive showed the decrease of the number of living bacteria to reach $1.0 \times 10^5$.

The mechanism supporting the improvement of preservability given by the present invention is not clearly understood at present. One hypothetical assumption induced from the fact that the number of deceased bacteria increases when the water content of starch or the like exceeds 5%, is as follows: Since the hygroscopicity of the additive such as starch that has been dehydrated and dried to reach the water content of not more than 4% is higher than that of the freeze-dried bifidobacterium powder, the water contained in a trace amount in a basic compounding material, such as sugar, is inhibited to transfer into freeze-dried bifidobacterium powder under the preservation condition at 37° C. Thus, the amount of water introduced in the vicinity of the bacteria is kept at a low level, thereby supressing the movement of molecule in the bacterium.

The present invention is further illustrated by the following Examples:

EXAMPLE 1

*Bifidobacterium infantis* S-12, ATCC No. 15697, was anaerobically cultured in a medium containing 5% of defat milk, at 37° C. for 18 hours, and the bacterial mass was collected by centrifuge. The collected mass was dispersed under anaerobical conditions in a dispersing medium containing 10% of skim milk, and freeze-dried to produce the bifidobacterium powder of a water content of not more than 3%.

Separately, a basic compounding material consisting of 95 parts of sugar powder, 1 part of gelatin, and 4 parts of water was kneaded in a twin arm mixer, supplied into a roller-type extruding granulating machine, and dried with hot air at 60° C. for 45 min. to form granules.

90.3 parts of the thus produced granules were mixed with 7 parts of corn starch adjusted to have the water content of approximately 0.5% under hot-air drying, 0.2 part of a previously prepared bifidobacterium powder, and 2.5 parts of tartaric acid, powdery flavor, etc. The mixture was molded under compression in a rotary-type tablet machine to form confectionery tablets.

The number of the bifidobacterium was determined directly after the formation of tablets to be $2 \times 10^8$ per 1 g. of the confectionery tablet. The confectionery tablet was stored at 37° C. for 3 months and then determined to be $8.2 \times 10^7$ of the living bacteria per 1 g. of the confectionery tablet.

In contrast to the above-described results, a confection formed into tablet made from a mixture of the aforementioned granulated basic compounding material without corn starch and the aforementioned bifidobacterium powder contained only $1.5 \times 10^5$ of the living bacteria per 1 g. of the confectionery tablet under the same conditions as described in the above.

Accordingly, it is concluded that the confectionery tablet of the present invention has excellent preservability.

EXAMPLE 2

81.8 parts of the granules produced in the same manner as in Example 1 were mixed with 15 parts of dry defat milk powder adjusted to have a water content of 1.0% by weight under hot-air drying, 0.2 part of the bifidobacterium powder produced in the same manner as in Example 1, and 3 parts of citric acid, powdery flavor, etc. The mixture was processed in the same manner as in Example 1 to give confectionery tablets.

The number of the bifidobacterium was determined to be $1.0 \times 10^8$ per 1 g. of the confectionery tablets. The confectionery tablets were stored at 37° C. for 3 months and then determined to show $4.5 \times 10^7$ of the living bacteria per 1 g. of the confectionery tablet.

EXAMPLE 3

| | |
|---|---|
| Crystalline glucose | 92 parts |
| Gelatin | 1 part |
| Water | 7 parts |

The above-mentioned materials were kneaded in a twin arm mixer, supplied into a roller-type extruding granulating machine, and dried with hot air at 60° C. for 60 min. to form granules. 93.8 parts of the thus obtained granules were mixed with 3 parts of a dry Pindex #5 prepared by drying Pindex #5 (DE value: 33, available from Matsutani Kagaku Co., Ltd., Japan) with hot air to adjust to a water content of 0.2% by weight, 0.2 part of the bifidobacterium powder prepared in the same manner as in Example 1, and 3 parts of citric acid, powdery flavor, etc. The mixture was then processed in the same manner as in Example 1 to give confectionery tablets.

The number of the bifidobacterium was determined to be $5 \times 10^7$ per 1 g. of the confectionery tablets. The confectionery tablets were stored at 37° C. for 3 months and then determined to be $1.2 \times 10^7$ of the living bacteria per 1 g. of the confectionery tablets.

EXAMPLE 4

81.8 parts of the granules produced in the same manner as in Example 1 were mixed with 7.5 parts of dry Pindex #5 prepared by drying Pindex #5 (DE value: 33, available from Matsutani Kagaku Co., Ltd., Japan) with hot air to adjust to a water content of 0.2% by weight and, 7.5 parts of potato starch adjusted to have a water content of approximately 0.5% under hot-air drying, 0.2 parts of bifidobacterium powder produced in the same manner as in Example 1, and 3 parts of citric acid, powdery flavor, etc. The mixture was processed in the same manner as in Example 1 to give confectionery tablets.

The number of bifidobacterium was determined to be $1.0 \times 10^8$ per 1 g. of the confectionery tablet.

The confectionery tablets were stored at 37° C. for 3 months and then determined to be $6.0 \times 10^7$ of the living bacteria per 1 g. of the confectionery tablet.

We claim:

1. The process for preparing bifidobacterium-containing confectionery tablets comprising a basic tablet-compounding material, a freeze-dried bifidobacterium, and between 3% and 15% by weight of at least one substance selected from the group consisting of starch, starch hydrolyzate and protein which contains not more than 4% of water, said process comprising mixing a freeze-dried living bifidobacterium powder with a basic compounding material separately prepared in a powdery state and between 3% and 15% by weight of at least one substance selected from the group consisting of starch, starch hydrolyzate and protein which contains not more than 4% of water, and forming tablets of said powdery mixture.

2. The process according to claim 1, wherein said at least one substance contains 0.2 to 1% of water.

3. The process according to claim 1, wherein said at least one substance is added in an amount of not less than 1% based on the total amount of the powdery mixture.

4. The process according to claim 1 or 2, wherein said at least one substance is starch selected from the group consisting of potato starch, sweet potato starch and corn starch containing 0.2 to 1.0% of water.

5. The process according to claim 1 or 2, wherein said at least one substance is starch hydrolyzate selected from the group consisting of dextrin, powdered starch syrup and maltose having DE of not more than 35 and containing 0.2 to 1.0% of water.

6. The process according to claim 1 or 2, wherein said at least one substance is protein selected from the group consisting of defat milk, casein and soybean protein containing 0.2 to 1.0% of water.

7. The process according to claim 5, wherein said starch hydrolyzate is dextrin having DE of 2 to 35.

8. The bifidobacterium-containing confectionery tablets produced in accordance with the process of claim 1.

* * * * *